United States Patent [19]

Duerr et al.

[11] Patent Number: 4,920,522
[45] Date of Patent: Apr. 24, 1990

[54] METHOD AND APPARATUS FOR MEASURING ELECTRICAL OR MAGNETIC FIELDS

[75] Inventors: Wilhelm Duerr, Erlangen; Ralph Oppelt, Uttenreuth/Weiher, both of Fed. Rep. of Germany

[73] Assignee: Siemens Aktiengesellschaft, Berlin and Munich, Fed. Rep. of Germany

[21] Appl. No.: 41,216

[22] Filed: Apr. 22, 1987

[30] Foreign Application Priority Data

May 6, 1986 [DE] Fed. Rep. of Germany ....... 3615197

[51] Int. Cl.⁵ .............................................. G01V 1/00
[52] U.S. Cl. ..................................... 367/134; 324/307
[58] Field of Search ................. 367/77, 134; 333/241, 333/242; 178/18; 340/708; 324/307, 318, 322

[56] References Cited

U.S. PATENT DOCUMENTS

| | | | |
|---|---|---|---|
| 3,564,398 | 2/1971 | Nelson | 324/310 X |
| 3,641,427 | 2/1972 | Pittman et al. | 367/134 |
| 4,045,767 | 8/1977 | Nishihara et al. | 367/134 |
| 4,102,195 | 7/1978 | Thompson et al. | 73/579 |
| 4,258,320 | 3/1981 | Schonstedt | 324/262 |
| 4,390,840 | 6/1983 | Ganssen | 324/309 |
| 4,506,224 | 3/1985 | Krause | 324/319 |
| 4,551,694 | 11/1985 | Biehl et al. | 333/263 X |
| 4,603,942 | 8/1986 | Chang et al. | 333/241 X |
| 4,628,264 | 12/1986 | Rzedzian | 324/322 |
| 4,677,428 | 6/1987 | Bartholow | 340/708 X |
| 4,689,761 | 8/1987 | Yurchenco | 364/708 |
| 4,737,712 | 4/1988 | Stormont et al. | 324/322 X |
| 4,763,075 | 8/1988 | Weigert | 324/318 |

FOREIGN PATENT DOCUMENTS

| | | |
|---|---|---|
| 0098426 | 1/1984 | European Pat. Off. . |
| 0105550 | 4/1984 | European Pat. Off. . |
| 0173130 | 6/1985 | European Pat. Off. . |
| 2126731 | 3/1984 | United Kingdom . |

OTHER PUBLICATIONS

"Communication Device for Patients Undergoing Nuclear Magnetic Resonance Imaging[1], " Ellis et al, Radiology, vol. 149, No. 3, 1983, p. 855.
"Anetnnas and Propagation Society Newsletter," IEEE, vol. 26, No. 5, Oct. 1984.
"British labs target enhanced EMC tests," Mitchell, Microwaves and RF, Jun. 1985 pp. 51-55.

Primary Examiner—Thomas H. Tarcza
Assistant Examiner—Tod Swann
Attorney, Agent, or Firm—Hill, Van Santen, Steadman & Simpson

[57] ABSTRACT

A method and apparatus for measuring electrical or magnetic fields, such as high-frequency alternating fields in a nuclear magnetic resonance tomography device, convert a test signal into a corresponding ultrasound signal, and transmit the ultrasound signal to a receiver, where the received signal is converted back into an electrical signal. The transmission path contains no metallic components and thus does not cause any disturbance in the field being measured.

7 Claims, 1 Drawing Sheet

METHOD AND APPARATUS FOR MEASURING ELECTRICAL OR MAGNETIC FIELDS

BACKGROUND OF THE INVENTION

1. Field of the Invention

The present invention relates to methods and structure for measuring electrical or magnetic fields, and in particular to a method and apparatus for measuring high-frequency (HF) alternating fields in a nuclear magnetic resonance device.

2. Description of the Prior Art

It is known that water-bonded hydrogen nuclei (protons) of an examination subject can be excited so as to precess from a preferred or equilibrium direction imposed by a fundamental magnetic field having a high static field strength. The nuclei are caused to precess by the application of high-frequency (HF) excitation pulses. After the end of an excitation pulse, the nuclei precess with a frequency dependent upon the strength of the fundamental field, and return to the equilibrium position due to their spin after a predetermined relaxation time. By computation or by direct measurement of the integral proton signals, an image can be produced from the three-dimensional spin density, or from the distribution of the relaxation times within a slice of the examination subject. Identification of a nuclear magnetic resonance signal resulting from this precessional motion with the location of its generation is undertaken by applying linear field gradients. These gradient fields are superimposed on the fundamental field, and are individually controlled such that excitation of the protons takes place only in the slice of interest. Such image presentation is known under various techniques such as NMR (nuclear magnetic resonance) tomography, Zeugmatography, spin imaging, or spin mapping.

The quality of the slice images produced is essentially determined by the signal-to-noise ratio of the induced nuclear magnetic resonance signal. Because this signal is in turn dependent on the fundamental field, and increases with frequency, high-frequency signals are desired given high-strength fundamental fields. For example, substantially uniform high-frequency magnetic fields having a high signal-to-noise ratio for signal excitation and reception can be generated by HF coils. The coils have a shared sheath of material having good electrical conductivity which is non-transmissive for high-frequencies and transmissive for low-frequencies. Fields oscillating in equiphase fashion arise in the full volume enclosed by the HF coils, within which the examination subject is disposed. Such an arrangement is described, for example, in German OS No. 31 33 432.

A requirement for this purpose, however, is that the high-frequency magnetic field be homogeneous. The existing high-frequency magnetic field must therefore be measured in advance with a measuring probe, the probe being used to measure the field at different locations so that the field strength dependent on the probe position can be determined. To limit measuring errors, the high-frequency magentic field should not be disturbed by the measuring instrument. The surface area of the metallic components of the measuring instrument must therefore be maintained small. In particular, the mechanical mount of the probe cannot contain any metallic carrier elements and cannot contain a metallic electrical line, for example a coaxial cable.

Probes for measuring electrical or magnetic fields in other environments are known wherein the mechanical mount is a rigid coaxial cable, which simultaneously serves as the electrical signal line. Due to the necessarily large longitudinal extent of such a metallic mount or signal line, the introduction of this probe into the field to be measured disturbs the high-frequency electromagnetic field.

Probes for measuring local antenna fields are also known wherein the signal read-out is made optically through optical fibers, as described in "British Labs Target Enhanced EMC Tests," Mitchell, Microwaves and RF, June 1985, pages 51–55. In order to convert the measured electrical signals into optical signals, however, a relatively complicated interface having an integrated power supply is required. The metallic extent thereof amounts to a number of centimeters in at least one direction. Such an optical signal read-out arrangement is thus unsuitable, for example, for nuclear magnetic resonance measurements.

SUMMARY OF THE INVENTION

It is an object of the present invention to provide a method and apparatus for measuring electrical or magnetic fields which permits precise vectorial measurements of the fields in terms of magnitude and direction to be made without significantly disturbing the field being measured.

It is a further object of the present invention to provide such a method and apparatus wherein the probe has the same dielectric and magnetic properties as the medium within the measuring volume.

The above objects are achieved in accordance with the principles of the present invention in a method and apparatus wherein the test signal is converted into a corresponding ultrasound signal which is transmitted to a receiver, and at the receiver is re-converted into an electrical signal. The ultrasound transmission path contains no metallic parts, and the field disturbance due to this measuring system is thus correspondingly low. The extent of the required measured value pick-up together with the allocated ultrasound transmission transducer is limited to a few millimeters.

In some application, a modulation of the measuring field may be preferable for measuring fields having an extremely high-frequency. In accord with a further embodiment of the method, the high-frequency electromagnetic field is amplitude modulated using a low-frequency test signal at which the signal transmission path operates, so that the measuring probe is independent of the frequency of the field to be measured and can be utilized for a broad frequency range.

The field disturbance caused by the measuring probe is substantially negligible. The method can therefore preferably be employed in nuclear magnetic resonators, or for measuring the local range of antennas. It is also suitable for vectorial measurement of electromagnetic fields. The measuring probe may be in the form of a loop for measuring a vector component of the magnetic field, and in the form of a small rod dipole for measuring a vector component of the electrical field. The remaining field components can be acquired by turning the measuring probe.

In one embodiment, the signal pick-up has an ultrasound transmission transducer allocated thereto and a non-metallic acoustic waveguide is provided as the transmission path. An ultrasound reception transducer is disposed at the end of the transmission path, the ultrasound reception transducer reconverting the transmitted sound signal into a corresponding electrical signal.

DESCRIPTION OF THE PREFERRED EMBODIMENTS

Figure 1:
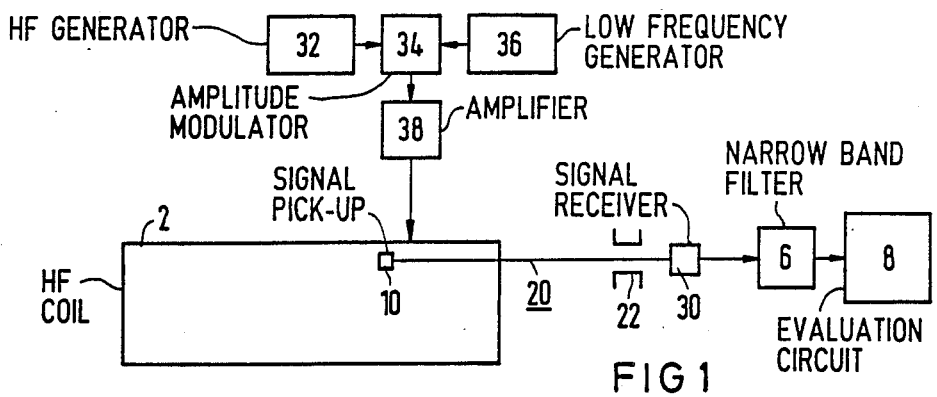
FIG. 1 is a schematic block diagram of an apparatus constructed and operating in accordance with the principles of the present invention.

An apparatus constructed in accordance with the principles of the present invention, and operating according to the method disclosed herein, is schematically shown in FIG. 1. This apparatus is suitable, for example, for use in producing slice images of an examination subject in a nuclear magnetic resonance tomography device. For this purpose, it is necessary to fashion a high-frequency coil 2 such that a field arises in the interior thereof which is as uniform as possible. For measuring this field, a measuring apparatus including a signal pick-up 10, which contains an ultrasound transmission transducer, a transmission path 20 consisting of a nonmetallic acoustic waveguide, and a signal receiver 30 including an ultrasound reception transducer are provided. The transmission path 20 is displacably held in a mount 22 and projects into the measuring volume of the high-frequency coil 2 in a self-supporting manner.

In a preferred embodiment, the high-frequency coil 2 receives an amplitude-modulated HF signal. For this purpose, an HF generator 32 is provided which generates a signal at, for example, 85 MHz. The output of the generator 32 is modulated by an amplitude modulator 34 using the signal of a low-frequency generator 36, the generator 36 providing an output signal at a frequency of, for example, 101.3 KHz. The output of the modulator 34 is supplied to the HF coil 2, through an amplifier 38 if necessary.

The signal receiver 30 is followed by a narrow-band filter 6 for the frequency of the low-frequency generator 36, the output of which is supplied to an evaluation circuit 8 which may be, for example, a volt meter.

Figure 2:
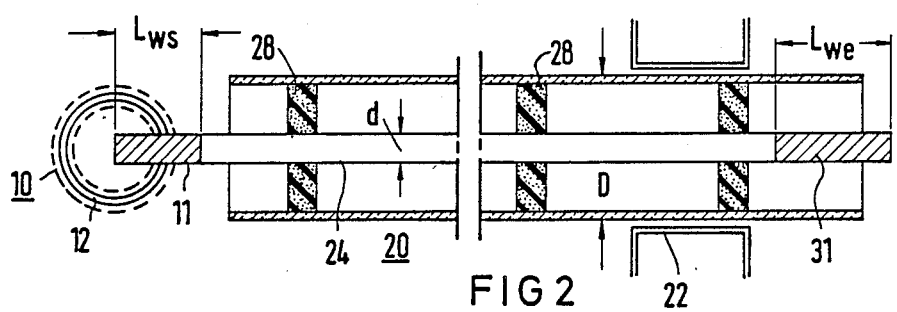
FIG. 2 is a side sectional view of one embodiment of a signal transmission path in the apparatus of FIG. 1.

One embodiment of a suitable transmission path 20 is shown in FIG. 2. The signal pick-up 10 (of which only the ultrasound transmission transducer 11 having a measuring loop 12 is shown) converts the picked-up measured signal into a corresponding ultrasound signal. The ultrasound signal is conducted via an acoustic waveguide 24 to the signal receiver, of which only the ultrasound reception transducer 31 is shown in the drawing. The ultrasound transducer 31 preferably has a length in the transmission direction of $L_{we}$ of, for example, about 22 mm. The acoustic waveguide 24 has a thickness d of, for example, about 2 mm and is concentrically surrounded by an exterior tube 26 having an outside diameter D of, for example, about 6 mm and a wall thickness of, for example, about 1 mm. The exterior tube 26 is acoustically insulated from the acoustic waveguide 24 by a plurality of acoustic insulators 28. The rod-shaped acoustic waveguide 24 consists of a material having high acoustic quality and a low dielectric constant, such as glass or plexiglass, preferably silica glass. The diameter of the acoustic waveguide 24 is essentially defined by that which is necessary to make the waveguide self-supporting for the distance from the signal pick-up 10 to the mount 22. The exterior tube 26 functions as a carrying element, and thus consists of a material having high mechanical strength and a low dielectric constant, preferably silica glass or plastic as well. The rings provided as acoustic insulators 28 consist of an acoustically soft substance, for example cellular material.

The ultrasound signals are conducted from the HF coils 2 using the acoustic waveguide 24 of the transmission path 20, which simultaneously serves as a probe mount, and are then reconverted into electrical signals at the ultrasound reception transducer 31. As a consequence of the finite length of the acoustic waveguide 24, the waveguide 24 acts as an acoustical resonator in continuous-wave operation. Its longitudinal oscillatory mode spacing, i.e., the frequency spacing of its natural resonances, is established by the length of the waveguide and the speed of sound therein. The exact length of the acoustic waveguide 24 is preferably selected for achieving high sensitivity so that one of its natural resonant frequencies is the same as the frequency of the electromagnetic alternating field to be measured. The natural resonance of the two ultrasound transducers also preferably at least approximately coincide with this frequency.

In the embodiment of the signal pick-up 10 of FIG. 2 for measuring magnetic fields, the ends of the measuring loop 12 (which may be provided with a shielding as indicated with dashed lines) are connected to the electrodes (not shown in detail) of the ultrasound transmission transducer 11. The transmission transducer 11 has a length $L_{ws}$ in the transmission direction of, for example, about 7 mm. The transducer 11 converts the picked-up electrical signal into a corresponding acoustic signal having the same frequency and transmits the acoustic signal to the receiver 30 through the waveguide 24.

Figure 3:
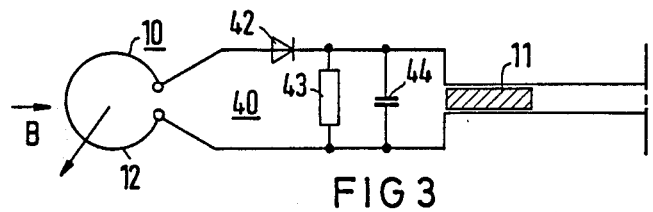
FIGS. 3, 4 and 5 are schematic circuit diagrams of different embodiments of a measured value pick-up for use in the apparatus of FIG. 1.

Because, due to its composition and the dimensioning of the transducers, the measuring instrument only transmits signal well which are within a predetermined frequency range. That is, the measuring instrument operates in a relatively narrow-band, and therefore a high-frequency modulation of the excitation signal of the high-frequency coil 2, and thus of the test signal, can be used in the embodiment shown in FIG. 1. The signal pick-up 10 of FIG. 3 is for this purpose provided with a corresponding demodulator 40. In this embodiment of the measuring instrument, particularly suited for measuring extremely high-frequency alternating fields, the test signal is modulated with a significantly lower frequency, for example in the range of from about 10 kHz through 1 MHz, preferably about 100 kHz, and is then demodulated. The demodulator 40 takes the modulation frequency out of the high-frequency signal. Only the low-frequency modulation signal is thus still transmitted, this being proportional in amplitude to the measured high-frequency field. When the optimum transmission frequency of the arrangement is identified at, for example, 101.3 kHz, the supplied frequency of the high-frequency coil 2 is precisely amplitude-modulated with this frequency. High-frequency fields of virtually any frequency can thus be measured using the same measuring instrument.

A passive mixer may, for example, be provided in combination with the current loop 12 operating as a magnetic dipole for measuring the magnetic induction B. The passive mixer includes a diode 42 and a resistor 43 having a resistance of, for example, 200 kohm. Under certain conditions, the mixer may also include a capacitor 44 is the capacitance of the ultrasound transmission transducer 11 is not sufficient for error-free demodulation. The signal pick-up 10 in this embodiment has only a small spatial extent of the ultrasound transmission transducer 11, not exceeding a few millimeters. Disfurbance of the field to be measured using the signal pick-up 10 is thus substantially impossible.

Figure 4:
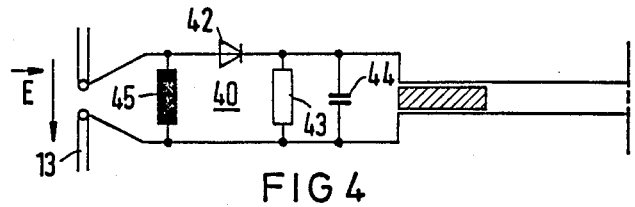

As shown in the embodiment of FIG. 4, the demodulator 40 may include an inductance 45 in combination with an electrical dipole 13 for measuring the electrical field strength, the inductance 45 bridging the poles (not shown in detail) of the dipole 13.

Figure 5:
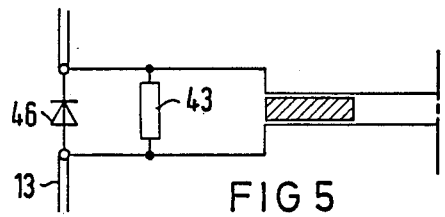

In another embodiment of a signal pick-up 10 as shown in FIG. 5, which also uses the electrical dipole 13, the demodulator 40 includes a diode 46 arranged in the dipole 13 and having a resistor 43 connected in parallel therewith.

Instead of the passive demodulators shown in FIGS. 3 through 5, active mixers may also be provided if needed, particularly for measuring relatively weak magnetic and electrical fields. Such active mixers, however, require an additional power supply, for example, a battery, which correspondingly increases the volume of the signal pick-up 10.

Although modifications and changes may be suggested by those skilled in the art it is the intention of the inventors to embody within the patent warranted hereon all changes and modifications as reasonably and properly come within the scope of their contribution to the art.

We claim as our invention:

1. A method for measuring an electric or magnetic field comprising the steps of:
   introducing a magnetic or electric dipole probe into a field to be measured which generates an electric signal characteristic of at least one parameter of said field;
   converting said electric signal into a corresponding ultrasound signal;
   transmitting said ultrasound signal to an ultrasound receiver remote from said probe; and
   re-converting the received ultrasound signal into an electric signal capable of evaluation.

2. A method as claimed in claim 1, wherein said field to be measured is a high-frequency alternating field generated by an excitation signal, and comprising the additional steps of:
   modulating said excitation signal with a low frequency signal;
   demodulating said electric signal generated by said probe to obtain a low-frequency demodulation signal having an amplitude proportional to said electric signal; and
   converting and transmitting said demodulation signal.

3. An apparatus for measuring electric or magnetic fields comprising:
   a probe including a magnetic or electric dipole capable of introduction into a field to be measured, said probe generating an electric signal characteristic of at least one parameter of said field;
   an ultrasound transmission transducer connected to said probe which converts said electric signal from said probe into a corresponding ultrasound signal;
   an ultrasound reception transducer disposed remote from said ultrasound transmission transducer; of said ultrasound transmission transducer and said ultrasound reception transducer which transmits said ultrasound signal therebetween, said ultrasound reception transducer re-converting the received ultrasound signal into an electric signal capable of evaluation.

4. An apparatus as claimed in claim 3, wherein said field to be measured is a high-frequency alternating field modulated by a low-frequency signal, and wherein said apparatus further comprises means for demodulating said electric signal generated by said probe to obtain a low-frequency demodulation signal having an amplitude proportional to said electric signal, and wherein said demodulation signal is converted into said ultrasound signal and transmitted by said means for transmitting.

5. An apparatus as claimed in claim 3, wherein said means for transmitting comprises:
   an acoustic waveguide consisting of a material having high acoustic quality and a low dielectric constant;
   an exterior tube coaxial with and surrounding said acoustic waveguide, said exterior tube consisting of a material having high mechanical strength and a low dielectric constants; and
   a plurality of sound insulators disposed between said acoustic waveguide and said exterior tube which support said waveguide within said tube.

6. An apparatus as claimed in claim 5, wherein each of said acoustic insulators is a ring of cellular material.

7. An apparatus as claimed in claim 3, wherein said measuring probe is a loop.

* * * * *